United States Patent [19]

Ono et al.

[11] Patent Number: 5,198,224

[45] Date of Patent: Mar. 30, 1993

[54] POLYPEPTIDE THIN FILM

[75] Inventors: Mitsunori Ono; Naoyuki Nishikawa, both of Kanagawa, Japan

[73] Assignee: Fuji Photo Film Co., Ltd., Kanagawa, Japan

[21] Appl. No.: 614,484

[22] Filed: Nov. 16, 1990

[30] Foreign Application Priority Data

Nov. 17, 1989 [JP] Japan .................. 1-299160

[51] Int. Cl.$^5$ .................. A61K 9/127; C08G 69/10; C07F 9/10
[52] U.S. Cl. .................. 424/450; 428/402.2; 428/338; 554/80; 554/84; 530/345; 528/328
[58] Field of Search .............. 428/402.2, 338; 424/450; 260/403, 404, 407; 530/345, 359, 402; 528/328; 554/80, 84

[56] References Cited

U.S. PATENT DOCUMENTS

| | | | |
|---|---|---|---|
| 4,485,045 | 11/1984 | Regen | 260/403 |
| 4,861,521 | 8/1989 | Suzuki et al. | 260/403 |
| 4,921,644 | 5/1990 | Lau et al. | 264/4.1 |
| 5,095,090 | 3/1992 | Ono et al. | 528/328 |
| 5,097,016 | 3/1992 | Ishii et al. | 530/350 |
| 5,138,026 | 8/1992 | Miyasaka et al. | 528/328 |
| 5,141,751 | 8/1992 | Tomikawa et al. | 424/450 |

FOREIGN PATENT DOCUMENTS

| | | | |
|---|---|---|---|
| 186211 | 7/1986 | European Pat. Off. | 260/403 |
| 1129190 | 6/1986 | Japan | 260/403 |
| 2283986 | 12/1987 | Japan | 260/403 |
| 3187842 | 7/1988 | Japan | 260/403 |

OTHER PUBLICATIONS

Hawley's Condensed Chemical Dictionary, 11th ed., (1987) p. 909.

Primary Examiner—Robert L. Stoll
Assistant Examiner—John M. Covert
Attorney, Agent, or Firm—Sughrue, Mion, Zinn, Macpeak & Seas

[57] ABSTRACT

A polypeptide thin film produced by polymerizing a monomolecular film or a built-up film comprising an amphipatic phospholipid compound, wherein the amphipatic phospholipid compound has a hydrophobic portion and a hydrophilic portion having an amino acid ester structure in the molecule, the amino acid ester structure containing a splitting-off group with a pKa value of the conjugated acid thereof being 16 or below.

8 Claims, 1 Drawing Sheet

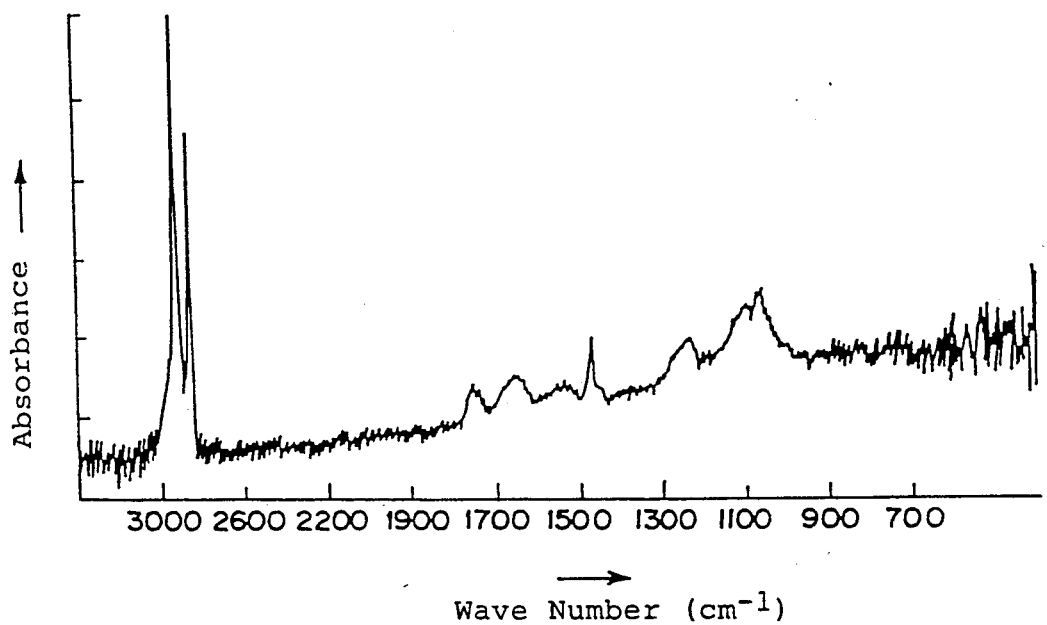
Fig. 1-B
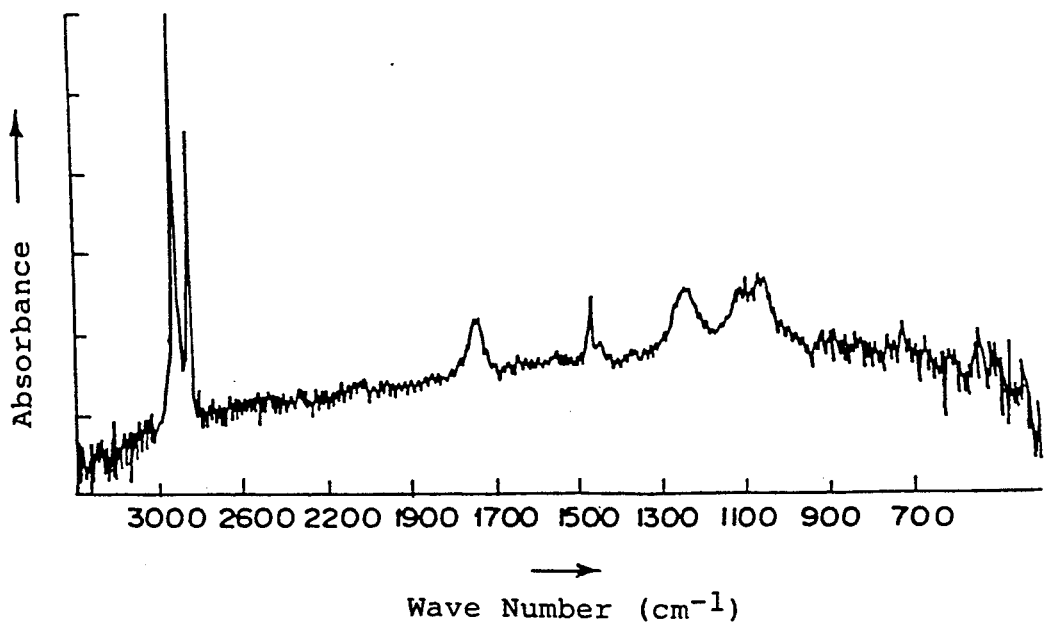

POLYPEPTIDE THIN FILM

FIELD OF THE INVENTION

The present invention relates to an ultra-thin film comprising a molecular polymer which is oriented. More particularly, the present invention relates to an ultra-thin film of an amino acid phospholipid polymer containing peptide bonds which have excellent biocompatibility.

BACKGROUND OF THE INVENTION

Because of its extreme thinness and elaborateness, a molecular assembly such as a monomolecular film (monolayer) which has a molecular arrangement or a built-up film (monolayers, i.e., multilayer) that comprises laminating a plurality of monolayers is quite versatile and has uses in applications as a material for electronics device use and as a material for surface protection use, as well as an ultrafiltration film, a thin film for sensor use as a permeation controlling film for material delivery relying on the selective permeability of gaseous molecules and ions of the molecular assembly.

A phospholipid is a main component of a cell biomembrane. In a biomembrane, a phospholipid forms a double layer structure having a bimolecular structure and performs many functions which are essential for various vital processes. In addition, it is known that, when either of natural and artificial phospholipids is dispersed in water, it forms a closed vesicle, called a liposome, which is made of a bimolecular membrane which is molecularly oriented. Attempts have been made to apply liposomes to drug delivery and artificial blood systems in medical science and pharmacology, as well as to production of artificial cells and microcapsules. In addition to the above-described applications as a monolayer and a multiple layer, application of the molecular assembly to medical materials has also been attempted due to the biocompatibility of liposomes.

The Langmuir-Blodgett (LB) method is commonly known as a method for forming an monomolecular film at a gas-liquid interface and building up the films on a support material. Recently, the use of various LB film prepared with this method has been expending in many field as organic ultrathin films (cf. Solid Physics (Japanese), vol. 17, No. 12, p. 45 (1982)).

Although the molecular assemblies including LB films and liposomes can be used to perform various functions based on the orientation of molecules and extreme thinness, they have disadvantages because the film can be easily destroyed due to its physically delicate structure and, in some cases, a less elaborate structure due to a structural defect in the film depending on its composition. As a result, preparation of films which are more elaborate by physically strengthening the film structure of these molecular assemblies is a subject to be studied.

One effective means to physically strengthen the film structure of these molecular assemblies is cross linking or polymerization of molecules. With regard to the polymerization of molecular assemblies such as LB films and liposomes, commonly used polymerizable compounds and polymerization patterns have been summarized by H. Bader et al. in Advances in Polymer Science, vol. 64, p. 1 (1985) and by R. Buschl et al. in Macromol. Chem. Suppl., vol. 6, p. 245 (1984).

Studies on polymerizable amphipathic compounds became active in 1980s. In the early stage of these studies, unsaturated vinyl, diene and diacetylene derivatives were used as the polymerizable compound and the polymerization was performed by cleaving unsaturated bonds in the compound with the aid of ultraviolet (UV) rays or radiant rays such as $\gamma$-rays. Although the rigidity of the films was improved by these polymerization methods in most cases, it was difficult to maintain the order of molecular arrangement because of strains caused by the polymerization. As has been indicated in Macromolecule (edited by A. Laschewsky and H. Ringsdorf; vol. 21, p. 1936, 1988), only a small number of compounds can result in a polymer film having an excellent order of molecular arrangement because the orientation of a film is affected greatly by the length of the alkyl chain and the kind of terminal hydrophilic groups.

A. Laschewsky et al. have disclosed in J. Am. Chem. Soc., vol. 109, p. 788 (1987) that support of polymerization groups via spacer groups is necessary for the maintenance of the order of molecular arrangement order in the case of amphipathic compounds having various unsaturated bonds useful for the radiation polymerization and the like. Also, JP-A-57-159506 (the term "JP-A" as used herein means an "examined Japanese patent publication") discloses an example of the application of monomolecular and built-up polymer films to ultrafiltration films, by preparing these polymer films from an unsaturated compound (a surface active agent) using radiation polymerization.

These compounds with unsaturated bonds cause the following disadvantageous problems when they are subjected to the prior art radiation polymerization process. Firstly, since disordered structural arrangement and a random aggregation and deposition of molecules tend to occur in such a polymerization process, it is necessary to introduce a special molecular design such as insertion of spacer groups in order to prevent these problems. Secondly, application of ultraviolet rays or $\gamma$-rays results in the decomposition and denaturation of various additive which are frequently present with polymerizable amphipatic molecules. Thirdly, the biocompatibility of films obtained with this type of polymerization is very poor in general, resulting in the limitation of their application to living tissues as a film for use in the permeation control of drugs and the like and other films for biological use.

Consequently, techniques other than radiation polymerization, such as the formation of disulfide bonds by means of oxidation polymerization of dithiole, have been proposed for example in J. Am. Chem. Soc., vol. 109, p 4419 (1987). Radical polymerization of the foregoing compounds with unsaturated bonds in the presence of an initiator may also be useful. In the technique, however, the use of an initiator is essential at the time of the polymerization. Therefore, not only is a process for the removal of the initiator from the film system after completion of the polymerization is required, but also the effect of the initiator e.g., as an oxidation-reduction agent, on substances also present is a problem.

Examples in which the biocompatibility of film was improved by a modification of polymerization systems include methods for self-condensation polymerization of molecular films composed of long chain alkyl derivatives of amino acids have been proposed in Macromol. Chem. Rapid Commun., vol. 3, p. 167 (1982) and in Thin Solid Films, vol. 133, p. 39 (1985) and a method for condensation polymerization of similar derivatives using carbodiimide as a condensation agent has been proposed in J. Am. Chem. Soc., vol. 108, p. 487 (1986). These methods, however, have certain disadvantages such as an extremely slow condensation reaction in the case of a self-condensation polymerization and residual condensation agent and by-products where a condensation agent is used.

Methods for polymerizing a diester phosphate monomer derived from a methacrylic acid ester in the presence of a polymerization initiator and methods for connecting a phospholipid analogue with the side chains of a synthetic polypeptide have been proposed in, .for example, Makromol. Chem., vol. 178, p. 2963 (1977), Makromol. Chem., vol. 179, p. 2349 (1978), Makromol. Chem. Rapid Commun., vol. 6, p. 285 (1985) and J. Makromol. Sci. Chem., vol. A25, p. 115 (1988) to prepare analogous biocompatible phospholipid films. By these methods, however, it is difficult to obtain a film which has a similar molecular orientation and arrangement to those of a natural biological membrane using these methods. In addition, the structure of these phospholipid analogous differs greatly from that of the phospholipid forming the biomembrane.

SUMMARY OF THE INVENTION

An object of the present invention is to overcome the above-described problems of the prior art. Another object of the present invention is to provide a first thin polymer film with an excellent molecular arrangement which can be obtained without using radiation and polymerization initiators and a process for producing a material carrying the first thin polymer film, a second thin polymer film which is obtained in such manner that the polymerization proceeds naturally at a high yield by self-polymerization and a process for producing a material carrying the second thin polymer film, and a third thin polymer film in which phospholipid side chains have a similar molecular orientation and arrangement to those of the natural biological membrane and which has excellent biocompatibility.

Other objects and advantages of the present invention will be made apparent as the description progresses.

The objects of the present invention are accomplished by a polypeptide thin film produced by polymerizing a monomolecular film or a built-up film comprising an amphipathic phospholipid compound, wherein the amphipathic phospholipid compound has a hydrophobic portion and a hydrophilic portion having an amino acid ester structure in the molecule, the amino acid ester structure containing a splitting-off group with a pKa value of the conjugated acid thereof being 16 or below.

BRIEF DESCRIPTION OF THE DRAWINGS

FIG. 1-A shows the infrared absorption spectrum of the product, after a polymerization process (37° C., 15 hours), of a monomolecular film of an amphipathic phospholipid compound which is represented hereinafter as formula (I)

(illustrative example I-5;

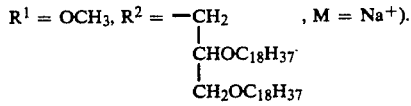
, M = Na$^+$).

FIG. 1-B shows the infrared absorption spectrum of a monomolecular film before polymerization.

DETAILED DESCRIPTION OF THE INVENTION

The present invention provides a polypeptide thin film produced by polymerizing a monomolecular film or a built-up film comprising an amphipathic phospholipid compound, wherein the amphipathic phospholipid compound has a hydrophobic portion and a hydrophilic portion having an amino acid ester structure in the molecule, the amino acid ester structure containing a splitting-off group with a pKa value of the conjugated acid thereof being 16 or below.

The polymerized monomolecular film or built-up film of the present invention comprises a main polymerized chain formed from a polypeptide, that is, a series of amide bond of amino acids, with phospholipid side chains. These ultra-thin films can be adhered to a supporting substrate using monolayer coating including the LB method.

The term "built-up film" as used herein and in the appended claims is intended to include a bimolecular membrane of closed vesicles which are made of the bimolecular membrane (liposomes). Accordingly, the term "polypeptide thin film" as used herein and in the appended claims includes liposomes formed by polymerization of closed bimolecular membranes made of the phospholipid compound of the present invention.

In the thin polymer film of the present invention, an amphipathic amino acid derivative having a reactive, namely electrophilic, ester group forms the structure of the amide bonding though the following condensation polymerization reaction;

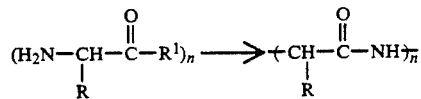

wherein n is an integer of 2 or more and R is a phospholipid residue, with R$^1$ being described hereinafter).

Techniques for forming the thin polymer film of the present invention are described below.

For the formation of the thin polymer film of the present invention, polymerization may be performed either at a gas-liquid interface or on a support material.

With regard to gas-liquid interface polymerization, a monomolecular film of an amphipathic phospholipid monomer derived from the amino acid ester used in the present invention may be prepared on a water phase (subphase) in a monomolecular film preparation trough by developing the phospholipid monomer using an appropriate organic solvent, followed by allowing the thus formed monomolecular film to stand on the water surface for an appropriate time to complete the polymerization. Distilled water or salt solutions such as a buffer solution may be used as the water phase. Preferably, the pH of the water phase is controlled within the range of from 5 to 9, depending on the ester decomposition equilibrium constant of the monomer to be used.

Temperature of the water phase is preferably in the range of from room temperature to 60° C., but a higher temperature within this range is more preferable for the purpose of accelerating the polymerization reaction. The surface pressure of a monomolecular film during the reaction is preferably kept at from 5 to 40 dyne/cm, more preferably at from 10 to 25 dyne/cm. The surface pressure is generally controlled at a constant level, but may be increased or decreased as the polymerization reaction progresses. After completion of the reaction, a monomolecular polymer film or a built-up polymer film can be prepared by transferring one or a plurality of the thus formed polymer films onto a hydrophilic or a hydrophobic support material using the Langmuir-Blodgett method (a vertical dipping method), a horizontal adhesion method or the like.

With regard to the second method, a monomolecular film of the above-described monomer of an amphipathic amino acid ester derivative is formed on the water surface, the resulting monomolecular film is transferred onto a support material using the above-described transfer means and then the thus transferred built up film is allowed to stand for an appropriate time on the support material for the polymerization reaction to occur. In the practice of this method, it is necessary to maintain the water phase at appropriate conditions which control the polymerization reaction, such as a low pH of 6 or lower and a low temperature, for the purpose of building up the monomolecular films on the support material prior to the polymerization. Polymerization of the monomers built up on the support material can be performed by accelerating the polymerization such as by heating, exposure to an alkaline gas ($NH_3$, for example) or immersion in an alkaline solution.

Of these two polymerization methods, the former gas-liquid interface polymerization is preferable in terms of the reaction capacity, but not necessarily in terms of reaction efficiency and the degree of polymerization achieved. These two methods, therefore, may be used appropriately depending on the stability of the monomer employed.

The amphipathic phospholipid compound derived from an amphipathic amino ester which can be used in the present invention is represented by the following general formula (I);

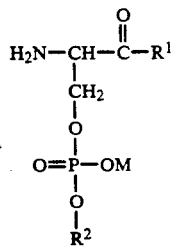
(I)

wherein $R^1$ is a splitting-off group with a pKa value of the conjugated acid thereof being 16 or below, $R^2$ is an organic group having one or more carbon atoms, M is a cation including hydrogen, and a portion of the formula, represented by the moiety

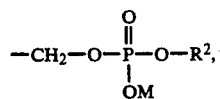

corresponds to the phospholipid residue R shown in the foregoing structure of the thin polymer film of the present invention.

More precisely, $R^1$ is preferably —X—$R^3$— wherein X is —O—, —S— or —N($R^4$)— where $R^4$ is a hydrogen atom, an alkyl group or an aryl group, and $R^4$ and $R^3$ may combine into a ring which may further contain a hetero atom such as nitrogen or may have an unsaturated bond). —O— is preferable for —X—.

Illustrative examples of $R^3$ include an aryl group (including substituted aryl groups, such as phenyl and naphthyl, with the substituent group being for example a nitro group and a halogen atom), an alkyl group (including substituted alkyl groups, such as methyl, benzyl and haloalkyl, with illustrative examples of haloalkyl being monochloroethyl, dichloroethyl and trichloroethyl), an acylamino group (for example, a N-methylacethylamino group and a N-methylbenzoylamino group), —N=$CR^5(R^6)$ (wherein $R^5$ and $R^6$ each represents a hydrogen atom, an alkyl group which may be substituted or an aryl group which may be substituted), an alkenyl group and an alkynyl group. A substituted or unsubstituted aryl group and a substituted or unsubstituted alkyl groups are preferred and those having 1 to 3 carbon atoms are more preferred as $R^3$.

Preferably, $R^2$ represents an alkyl group having at least 10 carbon atoms. Examples of the alkyl groups include a substituted alkyl group or an alkyl group connected to an unsaturated group. Preferred examples of $R^2$ include a n-dodecyl group, a n-hexadecyl group and a n-octadecyl group and, more preferably,

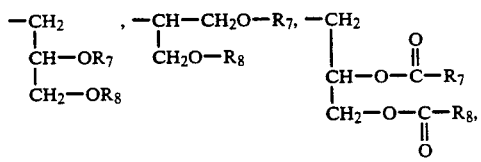

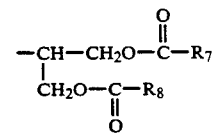

wherein $R^7$ and $R^8$ each represents an organic group having one or more carbon atoms, preferably an alkyl group (including a substituted alkyl group and an alkyl group connected to an unsaturated group), more preferably an alkyl group having at least 10 carbon atoms.

In addition, the amino acid ester portion (α-carbon atom) and $R^2$ in the amphipathic phospholipid derived from amino acid esters for use in the present invention are preferably be optically active.

Examples of preferred amino acid esters used in the present invention are given below by way of illustration and not by way of limitation.

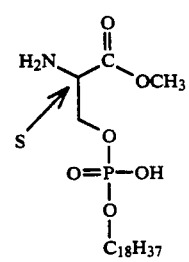
I-1

-continued
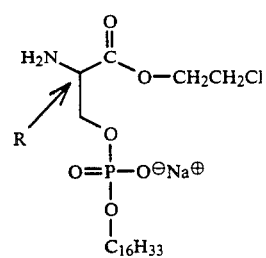
I-2
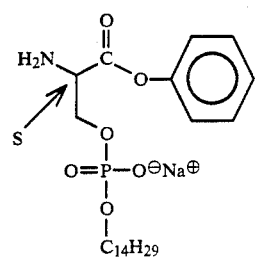
I-3
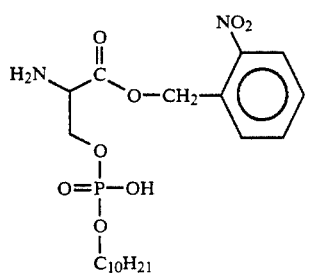
I-4
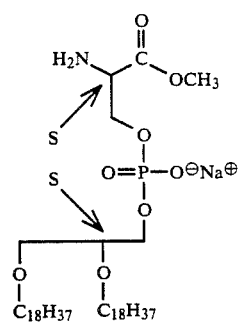
I-5
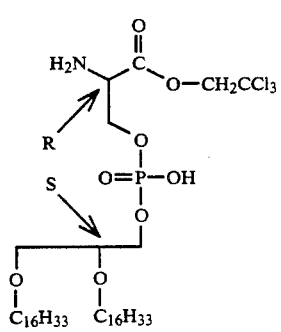
I-6
-continued
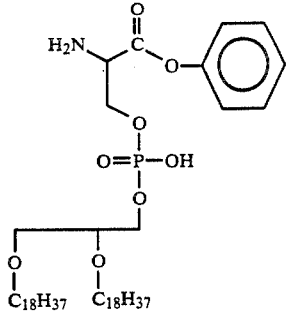
I-7
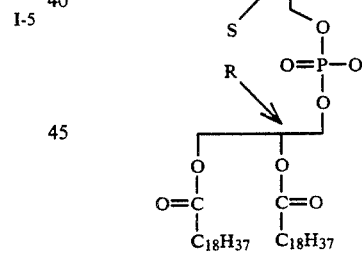
I-8
X = Cl, Br, I or F
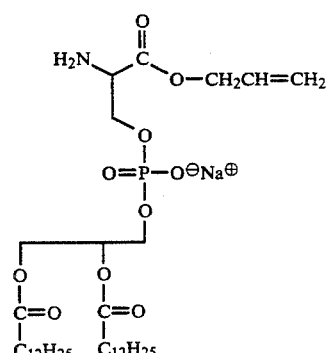
I-9
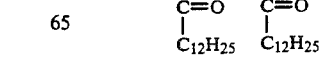
I-10

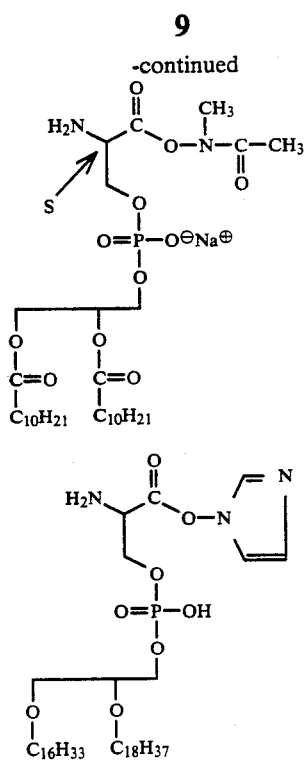

I-15

I-16 note: In the above, the symbols R and S designate a configuration around the carbon atom indicated.

Among them, Compounds I-1, I-9 and I-10 are more preferred.

The pKa value of the conjugated acid of the splitting group in each compound exemplified is shown below.

| Compound | pKa of Conjugated Acid of Splitting-off Group |
|---|---|
| I-1 | 16 |
| I-2 | 15 |
| I-3 | 10 |
| I-4 | 14 |
| I-5 | 16 |
| I-6 | 14 |
| I-7 | 10 |
| I-8 | 15 |
| I-9 | 13.5 |
| I-10 | 14 |
| I-15 | 9 |
| I-16 | 10 |

Typical examples of the synthetic techniques are given below by way of illustration and not by way of limitation.

The compound of the present invention as represented by the foregoing general formula (I) can, for example, be synthesized through the following synthetic pathway, although the present invention is not limited to the illustrated pathway.

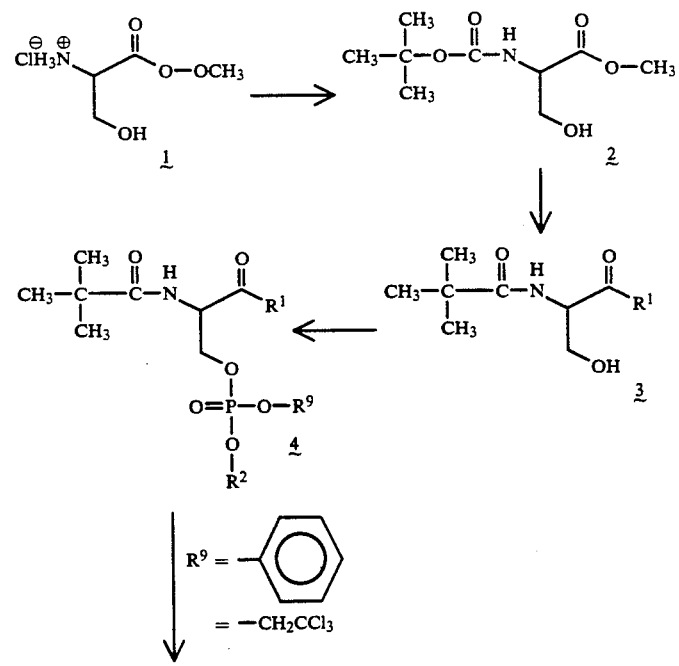

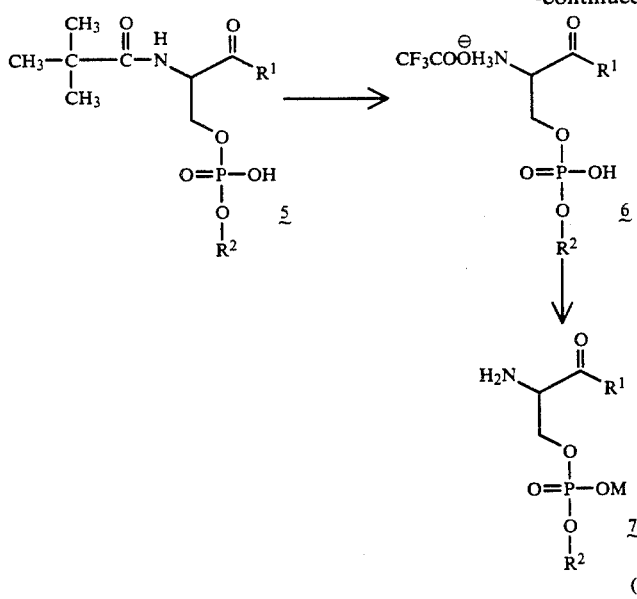
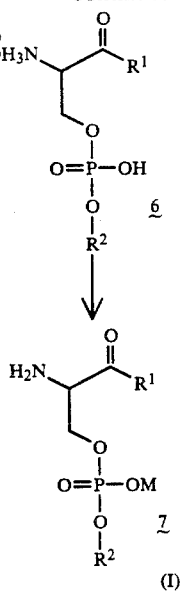

(I)

The following examples show the synthesis of Compound 7 shown above as a preferred compound of the present invention, wherein

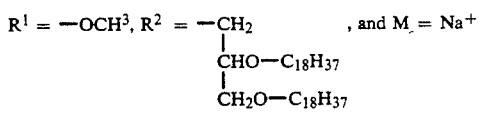

which corresponds to the foregoing illustrative example, namely, Compound I-5.

SYNTHESIS EXAMPLE 1

(Synthesis of Boc-1-serine methylester 2) (The term "Boc" as used herein means a t-butoxycarbonyl group.)

6.6 g (0.1 mol) of potassium hydroxide (purity, 85%) was dissolved in 150 ml of methanol. To this was added 15.6 g (0.1 mol) of 1-serine methylester hydrochloride and the mixture was stirred for 45 minutes. The resulting solution was mixed with 10.1 g (0.1 mol) of triethylamine and then with 21.8 g (0.1 mol) di-tert-butyl-dicarbonate which has been dissolved in 100 ml of tetrahydrofuran (THF) solution. After standing overnight, the THF in the mixture was distilled off under reduced pressure. A portion of ethyl acetate was added to the reside remaining after the distillation and the organic layer was washed with water. After drying with sodium sulfate, the solvent was distilled off. The resulting residue was then subjected to silica gel chromatography (hexane/ethyl acetate=7/3) to obtain 18.9 g (0.086 mol) of the Boc-1-series methylester 2 as a purified colorless liquid with the yield of 86%.

SYNTHESIS EXAMPLE 2

(Synthesis of phosphoric triester 4 wherein

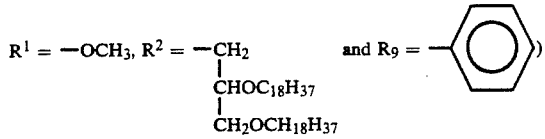

In 30 ml THF solution was dissolved 2.5 g (12 mmol) of phenylphosphodichloridate. To this was added dropwise 50 ml of THF solution in which 2.2 g (10 mmol) of the Boc-1-serine methylester 2 and 1.0 g (12 mmol) of methylimidazole had been mixed. After stirring for 3 hours, 150 ml of THF solution containing 5.9 g (10 mmol) of 1,2-o-distearyl-Sn-glycerol and 1.0 g (12 mmol) of methylimidazole was added dropwise to the stirred solution. After stirring for 6 hours, THF in the mixture was distilled off under reduced pressure. A portion of ethyl acetate was added to the residue remaining after the distillation and the residue was washed with water. After drying with sodium sulfate, the solvent was distilled off. The resulting residue was then subjected to silica gel chromatography to obtain 3.8 g (4.0 mmol) of the phosphoric triester 4 as a purified white waxy solid in a yield of 40%.

The following are examples of the analysis of the phosphoric triester product 4 produced as described above.

IR (KBr): 3400 cm$^{-1}$, 2925 cm$^{-1}$, 2850 cm$^{-1}$, 1755 cm$^{-1}$, 1720 cm$^{-1}$, 1600 cm$^{-1}$, 1470 cm$^{-1}$, 1280 cm$^{-1}$, 1060 cm$^{-1}$, 1030 cm$^{-1}$, 960 cm$^{-1}$, 770 cm$^{-1}$, 720 cm$^{-1}$ and 690 cm$^{-1}$.

Mass (M+Na)$^+$: 926

SYNTHESIS EXAMPLE 3

(Synthesis of 1,2-o-distearyl-Sn-glycerophosphatidyl-serine methyl ester 7)

In 50 ml of ethyl acetate was dissolved 0.5 g of the phosphoric triester 4 obtained in Synthesis Example 2 above. Hydrolysis of the compound 4 was performed under normal pressure in the presence of an Adams catalyst (PtO$_2$) to obtain quantitatively a white waxy solid of compound 5

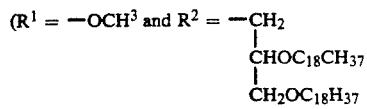

Compound 5 thus obtained was dissolved in 8 ml of dichloromethane and the resulting solution was mixed with 8 ml of trifluoroacetic acid. After stirring for 30 minutes, the solvent system was distilled off to obtain quantitatively the compound 6

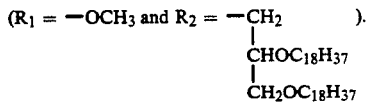

The thus obtained compound 6 was dissolved in chloroform and the solution was desalted using a saturated sodium hydrogen carbonate solution. The organic layer of the desalted solution was washed with water and then dried using sodium nitrate to obtain 250 mg of the compound 7

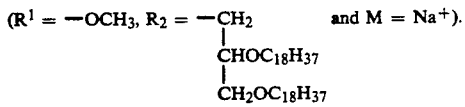

The following are examples of the analysis of the thus obtained compound 7.

IR (KBr): 3400 cm$^{-1}$, 2925 cm$^{-1}$, 2850 cm$^{-1}$, 1750 cm$^{-1}$, 1470 cm$^{-1}$, 1240 cm$^{-1}$, 1100 cm$^{-1}$, 1080 cm$^{-1}$, 840 cm$^{-1}$ amd 720 cm$^{-1}$.

Mass (M+)+: 800

Next, examples of the synthesis of another form of compound 7 are shown below, wherein

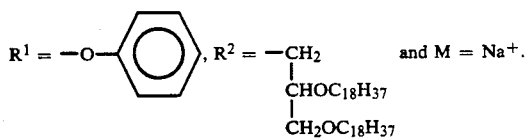

This form of the compound 7 corresponds to the foregoing illustrative example of the amino acid ester as represented by formula I-7.

SYNTHESIS EXAMPLE 4

(Synthesis of Boc-1-serine-phenylester 3 wherein

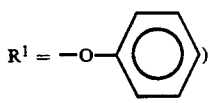

A mixture of 30 g (0.14 mol) of Boc-1-serine methylester, 58 g (0.69 mol) of dihydropyran and 600 ml of chloroform was further mixed with 2 ml of a THF solution containing 250 mg of p-toluenesulphonic acid and stirred for 3 hours at room temperature. After distilling off the solvent, an appropriate amount of chloroform was added to the remaining portion and the organic layer was washed with water. The organic layer was then dried with sodium sulfate and the solvent was distilled off under a reduced pressure. Next, 800 ml of methanol and 150 ml of 1N sodium hydroxide aqueous solution in that order were added to the remaining residue and the resulting mixture was stirred overnight. After distilling off the methanol, impurities in the resulting residue was extracted by adding ethyl acetate and water. The resulting water layer was then adjusted to a pH of 3 with a 15% citric acid aqueous solution and the reaction product was extracted with ethyl acetate. Thereafter, the organic layer was washed with water and dried using sodium sulfate and remaining ethyl acetate was distilled off under reduced pressure.

The resulting residue after the distillation was dissolved in 400 ml of THF and mixed with 26.6 g (0.16 mol) of carbonyldiimidazole. After stirring for one hour, 50 ml of a THF solution containing 13 g (0.14 mol) of phenol and 13.8 g (0.14 mol) of triethylamine was added dropwise to the mixture. After 4 hours of stirring, the solvent in the mixture was distilled off under reduced pressure and the reaction product in the resulting residue was extracted with ethyl acetate and water. Thereafter, the organic layer was washed with water and dried using sodium sulfate, the remaining ethyl acetate was distilled off under reduced pressure and the resulting residue was subjected to silica gel chromatography (hexane/ethyl acetate=8/2) to obtain 32 g of purified white solid.

The thus obtained white solid (32 g) was dissolved in 400 ml of THF, the resulting solution was mixed with 40 ml of an aqueous solution containing 4.6 g (0.018 mol) of pyridinium p-toluenesulphonate (PPTS) and the mixture was then stirred at 60° C. for 6 hours. After distilling off the solvent, the reaction product was extracted with chloroform and water, the resulting organic layer was dried using sodium sulfate and remaining chloroform was distilled off under a reduced pressure. Thereafter, the resulting residue was subjected to a silica gel chromatography to obtain 30 g of purified compound 3

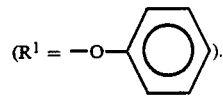

The thus obtained product was further subjected to a recrystallization process with a chloroform-hexane system to obtain compound 3

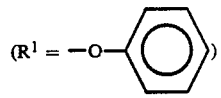

as 12.6 g (0.045 mol) of white powder (33% yield from Boc-1-serine methylester).

The following examples shows analysis of the thus obtained compound 3 product.

IR (KBr): 3375 cm$^{-1}$, 3275 cm$^{-1}$, 2960 cm$^{-1}$, 2925 cm$^{-1}$, 1770 cm$^{-1}$, 1700 cm$^{-1}$, 1600 cm$^{-1}$, 1490 cm$^{-1}$, 1400 cm$^{-1}$, 740 cm$^{-1}$ and 690 cm$^{-1}$.

SYNTHESIS EXAMPLE 5

(Synthesis of phosphoric triester 4 wherein

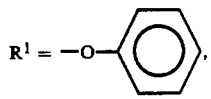

-continued $R^2 = -CH_2$ and $R^9 = -CH_2CCl_3$)
         |
         $CHOC_{18}H_{37}$
         |
         $CH_2OC_{18}H_{37}$ In 10 ml of THF was dissolved 1.3 g (0.5 mol) of trichloroethylphosphodichloridate. To this was added dropwise 10 ml of a THF solution in which 1.4 g (0.50 mol) of Boc-1-serine phenylester and 0.42 g (0.51 mol) of methylimidazole had been mixed. After stirring for one hour at room temperature, 2.95 g (0.50 mol) of 1,2-o-distearyl-Sn-glycerol and 0.42 g (0.51 mol) of methylimidazole was added to the stirred solution. After stirring for 4 hours, the THF in the mixture was distilled off under reduced pressure, the resulting residual portion was mixed with chloroform and washed with water. The resulting organic layer was dried using sodium sulfate and the remaining chloroform was distilled off under reduced pressure. The resulting residue was then subjected to silica gel chromatography (hexane/ethyl acetate=8/2) to obtain 0.98 g of the phosphoric triester 4

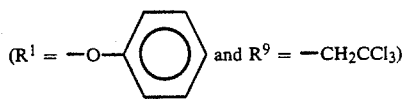

($R^1 = -O-\bigcirc$ and $R^9 = -CH_2CCl_3$)

as a purified white solid in a yield of 20%.

The following shows examples show analysis of the thus obtained phosphoric triester 4 product.

IR (KBr) 3400 cm$^{-1}$, 2925 cm$^{-1}$, 2850 cm$^{-1}$, 1780 cm$^{-1}$, 1720 cm$^{-1}$, 1600 cm$^{-1}$, 1500 cm$^{-1}$, 1460 cm$^{-1}$, 1300 cm$^{-1}$, 1200 cm$^{-1}$, 1160 cm$^{-1}$, 1120 cm$^{-1}$, 1035 cm$^{-1}$, 900 cm$^{-1}$, 720 cm$^{-1}$ and 695 cm$^{-1}$.

Mass (M+Na)$^+$: 1092

SYNTHESIS EXAMPLE 6

(Synthesis of 1,2-o-distearyl-Sn-glycerophosphatidyl-serine phenylester)

In 10 ml of THF was dissolved 0.26 g (0.24 mmol) of compound 4 obtained in Synthesis Example 5 above.

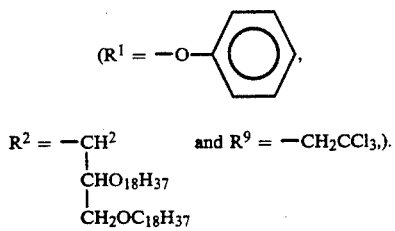

$R^2 = -CH^2$ and $R^9 = -CH_2CCl_3$,).
       |
       $CHO_{18}H_{37}$
       |
       $CH_2OC_{18}H_{37}$ To this was further added 9 ml of acetic acid, 1 ml of water and 1 g of zinc powder.

After stirring for one hour, the reaction solution was subjected to Celite filtration and the resulting filtrate was concentrated and mixed with chloroform and water. The organic layer of the mixture was then dried using sodium sulfate and chloroform remaining was distilled off under reduced pressure. Thereafter, the thus obtained white solid was washed with acetone to obtain 0.16 g of compound 5

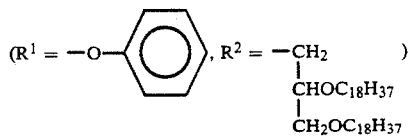

($R^1 = -O-\bigcirc$, $R^2 = -CH_2$ )
                        |
                        $CHOC_{18}H_{37}$
                        |
                        $CH_2OC_{18}H_{37}$ The solid compound 5 thus obtained (0.16 g) was dissolved in 2 ml of dichloromethane and the resulting solution was mixed with 2 ml of trifluoroacetic acid. After stirring for 30 minutes, the solvent system was distilled off and the resulting residue was dissolved in chloroform. Thereafter, the thus prepared solution was desalted at a low temperature using a saturated sodium hydrogen carbonate solution to obtain 50 mg of white waxy solid of compound 7

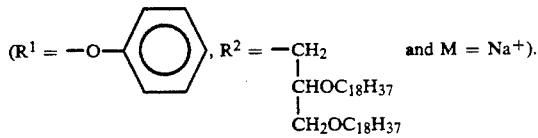

($R^1 = -O-\bigcirc$, $R^2 = -CH_2$ and $M = Na^+$).
                        |
                        $CHOC_{18}H_{37}$
                        |
                        $CH_2OC_{18}H_{37}$ The following examples show analysis of the thus obtained product.

IR (KBr): 3400 cm$^{-1}$, 2925 cm$^{-1}$, 2850 cm$^{-1}$, 1760 cm$^{-1}$, 1600 cm$^{-1}$, 1470 cm$^{-1}$, 1240 cm$^{-1}$, 1100 cm$^{-1}$, 1060 cm$^{-1}$, 760 and 720 cm$^{-1}$.

Mass (M-CF$_3$COO+Na)$^+$: 862 (TFA salt 6;

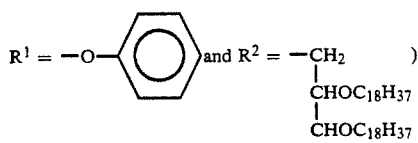

$R^1 = -O-\bigcirc$ and $R^2 = -CH_2$ )
                          |
                          $CHOC_{18}H_{37}$
                          |
                          $CHOC_{18}H_{37}$ Other compounds may be synthesized in the same manner as described above. All compounds represented by formula (I) decomposed gradually at around 70° C. because of their reactivities.

According to the present invention, suitable support material (substrate) on which a monomolecular film or a built-up film is coated may be selected from various organic resins and inorganic materials provided that the surface of these support materials has a hydrophilic or hydrophobic property. The support material may have a flat and even structure, a porous three-dimentional network structure or fibrous three-dimensional network structure.

Illustrative examples of flat and even materials include electrically conductive materials made of various metals and the like, glassy materials such as glass and quartz, various inorganic and organic crystals, inorganic semiconductors (SnO$_2$, In$_2$O$_3$, ZnO, TiO$_2$, WO$_3$, GaAs, Si and the like), organic semi-conductors, organic conductors, organic polymers, and complex materials thereof. An electrode and other sensors (field effect transducer and the like), which are connected with external electric circuits, may also be employed.

Porous materials are useful as the support material when the polyptide thin film of the present invention is to be used as permeation film or a filter. Illustrative examples of suitable porous materials include organic or inorganic microporous filters, cellulose resin films and various other porous polymer films.

With regard to a developing solvent for use in the formation of monomolecular film of the present invention, thus solution may be selected from conventional volatile non-polar organic solvents such as chloroform, dichloromethane, benzene, toluene and ether, as well as from mixtures of these solvents with polar hydrophilic solvents such as alcohols and water.

For the purpose of coating a monomolecular film on another film formed on a water surface or of coating it on a substrate or a support material, various building-up methods including the LB method can be empoyed. The LB method which is a vertical adhesion method is described in detail, for example, in J. Am. Chem. Soc., vol. 57, p. 1007 (1935), in Insoluble Monlayers at Liquid-Gas Interfaces (edited by G. L. Gains Jr., Interscience, New York, 1966) and in Material Technology (written in Japanese, edited by K. Fukuda, vol. 4, p. 261, 1986).

In addition to the LB method, various other techniques such as a horizontal adhesion method and a rotary adhesion method may be employed as the coating method. Examples of these techniques are disclosed, for example, in JP-A-60-189929 and in JP-A-61-42394. A built-up film may be obtained by repeating a coating process of coating a monomolecular film on a substrate. To achieve efficient build-up of films, a modified horizontal adhesion method as disclosed in JP-A-1-209245 or the continuous build-up methods disclosed in JP-A-60-209245 and the like may also be used.

With regard to the application of the peptide thin film of the present invention to liposomes, any of the well-known prior art techniques for the production (preparation) of liposomes, as well as a stable pleri-lamellar vesicle method (SPLV method) which has recently been reported by S. M. Gruner et al. in Biochemistry (vol. 24, p. 2833, 1985), can be used. Examples of suitable known techniques which can be used for the production (preparation) of liposomes include a vortexing method, an ultrasonic treatment method, a surface active agent treatment method, a reverse phase evaporation method (REV method), an ethanol injection method, an ether injection method, a pre-vesicle method, a French press extrusion method, a $Ca^{2+}$ fusion method, an annealing method, a freezing-thawing fusion method and a W/O/W emulsion method. These techniques are described in "Liposome" (written in Japanese, edited by S. Nojima, J. Sunamoto and K. Inoue, published by Nankodo in 1988; Chapter 2, page 21).

In producing liposomes, the compound of the present invention may be used alone, as an admixture of two or more compounds of the present invention or as a mixture with a known conventional liposome-forming material.

There are no special limitations in terms of hydrophilic property, water solubility and the like as to the material to be included into liposomes. The following materials are given as examples by way of illustration and not by way of limitation: carcinostatic agents such as a driamycin, actinomycin, mitomycin, 1-β-arabinofuranosyl cytosine, bleomycin and cisplatin; anti-viral agents such as interferon; antibiotic agents such as aminoglycosides (gentamycin for example) and β-lactams (sulbenicillin, cefotium and coefmenoxime); peptide hormone preparations such as TRH and insulin; enzyme preparations such as lysozyme, asparaginase and glycosidases; immunopotentiators such as muralyl dipeptide and muramyl tripeptide; and proteins such as immunoglobulins and various toxins.

The following Examples are given to further illustrate the present invention. Examples of the present invention are given below by way of illustration and not by way of limitation.

EXAMPLE 1

As an amphipathic amino acid methylester phospholipid, the Compound I-5 described above was dissolved in chloroform to a concentration of 1 mM and used as the developing solution. The thus prepared solution was developed on the water phase of $10^{-3}$ M phosphate butter (pH 7.4) at 37° C. using a Langmuir's film balance to produce a monomolecular film. Polymerization was performed by allowing the resulting monomolecular film to stand for 15 hours under a constant surface pressure of 15 dyne/cm using a belt-drive type barrier.

The thus polymerized monomolecular film was built up on a silicon wafer substrate by the LB method. Measurement of the FT-IR absorption spectrum of the resulting built-up film by the permeation method showed that the absorption which is characteristic of an ester (1750 cm$^{-1}$) was reduced and amide-characteristic absorption (1650 cm$^{-1}$ and 1550 cm$^{-1}$) appeared instead (as shown in FIGS. I-A and I-B), thus confirming production of the intended product.

The reaction ratio was found to be around 40%.

EXAMPLE 2

The polymerization process of Example 1 was repeated except that Compound I-7 described above was used as an amphipathic amino acid phenylester phospholipid. The reaction was accomplished almost completely after 2 hours of standing.

EXAMPLE 3

The following shows an example of the preparation of liposomes employing a thin film method using the peptide thin film of the present invention.

An eggplant type flask was charged with 10 mg of the Compound I-5 described above as an amphipathic amino acid methyl ester phospholipid and the compound was dissolved in 5 ml of chloroform. A thin film of the compound was prepared by distilling off the chloroform in the flask under reduced pressure using a rotary evaporator. After drying the thin film under reduced pressure, the film-containing flask was charged with 3 ml of distilled water, heated at 70° C. for 30 seconds in a water bath and then shaken for one minute using a Vortex mixer. This heating-mixing process was repeated three times to obtain liposomes having a mean particle size of around 1000 nm. The size of the thus obtained liposomes was decreased to a mean particle size of 300 nm by treating them with a bath type sonicator at 60° C. Electron microscopic observation of the morphology of these particles confirmed that they were liposomes.

EXAMPLE 4

Compound I-5 as described above was dispersed in a phosphate buffer (pH 7.4) containing 200 mM of 5(6) carboxylfluorescein (CF) in accordance with the Example 3. Gel filtration of the resulting liposomes confirmed that the interior of these liposomes was filled with the CF buffer.

While the invention has been described in detailed with reference to specific embodiments, it will be apparent to one skilled in the art that various changes and modifications can be made to the invention without departing from its spirit and scope.

What is claimed is:

1. A polypeptide thin film comprising a monomolecular film or a built-up film comprising an amphipathic phospholipid compound, wherein said amphipathic phospholipid compound has: (a) a hydrophobic portion comprising an organic group having only single bonds in the backbone, and (b) a hydrophilic portion having an amino acid ester structure in the molecule, said amino acid ester structure containing a splitting-off group with a pKa value of the conjugated acid thereof being 16 or below, wherein said amphipathic phospholipid compounds are joined covalently by amino bonding between the amino acid residues.

2. The polypeptide thin film of claim 1, wherein the amphipathic phospholipid compound is a compound represented by the general formula (I):

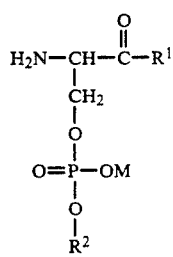
(I)

wherein $R^1$ is a splitting-off group with a pKa value of the conjugated acid thereof being 16 or below, $R^2$ is an organic group having one or more carbon atoms and no double bonds and M is a cation.

3. The polypeptide thin film of claim 2, wherein $R^1$ is —X—$R^3$—, wherein X is —O—, —S— or —N($R^4$), where $R^4$ is a hydrogen atom, an alkyl group or an aryl group, $R^3$ is a substituted or unsubstituted phenyl group or benzyl group, a substituted or unsubstituted alkyl group having 1 to 3 carbon atoms, an N-methylacetylamino group, an allyl group, a propargyl group, or —N=C$R^5$($R^6$), where $R^5$ and $R^6$ each represents a hydrogen atom, an alkyl group which may be substituted or an aryl group which may be substituted, and $R^3$ and $R^4$ may combine into a ring which may contain a hetero atom or an unsaturated bond; and $R^2$ is a substituted or unsubstituted alkyl group having at least 10 carbon atoms.

4. The polypeptide thin film of claim 2, wherein the amino acid ester portion and $R^2$ are optically active.

5. The polypeptide thin film of claim 1, wherein said film has a flat and even structure, a porous three-dimensional network structure or fibrous three-dimensional network structure.

6. The polypeptide thin film of claim 1, wherein said film is in the form of a liposome.

7. The polypeptide thin film of claim 6, wherein said liposome additionally contains at least one of a carcinostatic agent, an anti-viral, an antibiotic agent, a peptide hormone, an enzyme and immunoglobulin.

8. The polypeptide thin film of claim 5, wherein said amphipatic phospholipid compound is compound I-5:

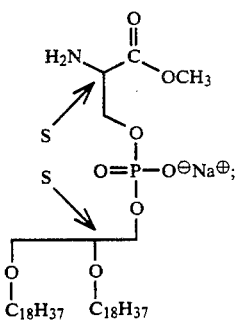

and wherein said film has a fibrous three-dimensional network.

* * * * *